US005124531A

United States Patent [19]

Ishiguro

[11] Patent Number: 5,124,531

[45] Date of Patent: Jun. 23, 1992

[54] ELECTRIC HEATER FOR HEATING A SELECTED PORTION OF WORKPIECE AND METHOD OF HEATING THE WORKPIECE BY THE HEATER

[75] Inventor: Fujio Ishiguro, Nagoya, Japan

[73] Assignee: NGK Insulators, Ltd., Japan

[21] Appl. No.: 547,232

[22] Filed: Jul. 3, 1990

[30] Foreign Application Priority Data

Jul. 5, 1989 [JP] Japan ........................ 1-173522

[51] Int. Cl.$^5$ ........................ F26B 3/30; A45D 20/40; F24C 7/00; A61M 5/06

[52] U.S. Cl. ........................ 219/200; 392/407; 29/610.1; 29/613; 338/262

[58] Field of Search ........................ 219/200-201, 219/386, 390, 521, 385, 339, 552, 338; 156/620.73; 422/250; 29/613, 619, 611, 615, 610.1; 338/260-270, 277, 296; 174/DIG. 8; 392/407, 416, 418, 422, 440

[56] References Cited

U.S. PATENT DOCUMENTS 3,378,672 4/1968 Blumenkranz ........................ 219/535
3,413,441 11/1968 Isobe et al. ........................ 219/390
3,475,592 10/1969 Berkl ........................ 219/535
3,769,484 10/1973 Stut et al. ........................ 156/620.73
3,979,625 9/1976 Roberts ........................ 29/611
4,020,791 5/1987 Reuschel et al. ........................ 219/390
4,055,219 10/1977 Orlandi et al. ........................ 219/390
4,078,910 3/1978 Dalgoutte ........................ 350/96.23
4,460,820 7/1984 Matsumoto et al. ........................ 219/535
4,695,335 9/1987 Lyall ........................ 219/535
4,711,989 12/1987 Yu ........................ 219/390
4,948,435 8/1990 Butler et al. ........................ 148/127

FOREIGN PATENT DOCUMENTS 2130555 12/1972 Fed. Rep. of Germany ...... 219/521
97907 2/1979 Japan ........................ 219/390
289522 2/1971 U.S.S.R. ........................ 219/390

*Primary Examiner*—Bruce A. Reynolds
*Assistant Examiner*—John A. Jeffery
*Attorney, Agent, or Firm*—Parkhurst, Wendel & Rossi

[57] ABSTRACT

An electric heater for heating a workpiece including at least one heat generating wire which generates heat upon application of an electric current thereto, and which has a diameter of not more than 1 mm. Each heat generating wire has a heating portion which is formed by bending so as to at least partially define a heating space. The workpiece to be heated by the electric heater is positioned relative to the heating space, such that the workpiece is spaced apart from the heating portion of the heat generating wire or wires.

17 Claims, 3 Drawing Sheets

ELECTRIC HEATER FOR HEATING A SELECTED PORTION OF WORKPIECE AND METHOD OF HEATING THE WORKPIECE BY THE HEATER

BACKGROUND OF THE INVENTION

1. Field of the Invention

The present invention relates in general to an electric heater used for heating a workpiece of a small size, which has both a portion which must be heated and a portion which must not be heated, and a method of heating the workpiece by means of such an electric heater. More particularly, the present invention is concerned with an electric heater which is suitably used for firing a protective glass for a platinum-film resistor used in a film element of an air-flow sensor, for example.

2. Discussion of the Prior Art

A platinum-film resistor is generally used in a film element of an air-flow sensor for detecting a flow rate of air stream. The platinum-film resistor is produced by attaching a pair of lead wires made of base metal, to opposite ends of a ceramic body having a platinum layer formed thereon by plating.

In producing the platinum-film resistor, the platinum plating layer formed on the ceramic body is secured by firing thereof to the ceramic body, and the base metal lead wires are connected by firing thereof to the platinum plating layer. Thereafter, the platinum plating layer on the ceramic body is coated with a glass, and the applied glass is fired, whereby a protective glass for protecting the platinum plating layer is formed on the ceramic body. It is generally recognized that the entire length of the platinum plating layer (ceramic body) to which a glass coating is applied is extremely short, e.g., in the neighborhood of 4–5 mm. Further, no means is known for effectively heating only the platinum plating layer coated with the glass. Under these situations, the firing of the glass has been conventionally effected by using a tubular furnace, which is constructed such that a heat generating element is wound around a ceramic tube made of alumina, for example, and which is adapted to heat the whole platinum-film resistor accommodated therein. Alternatively, the glass on platinum plating layer is fired in a box-like furnace which has a box-like body made of brick, on which a heat generating element formed of SiC, for example, is provided.

However, when the firing of glass is effected by heating the whole platinum-film resistor in the tubular or box-like furnace, it takes a long time for the furnace to be heated or cooled to a desired degree, since the furnace has a relatively large heat capacity. Further, since the firing temperature of the glass is extremely high, e.g., in the neighborhood of 800° C., the temperature in the furnace is maintained for a considerably long time above the temperature at which the lead wires are oxidized, (usually 400° C. or higher). Therefore, if only the platinum plating layer on the ceramic body is coated with a glass, and the glass is fired in the furnace with the lead wires being exposed to the atmosphere in the furnace, the lead wires undergo a change of color due to oxidation, and are even torn off in the worst case. For preventing the oxidation of the lead wires, nitrogen or hydrogen gas may be introduced into the furnace, so that the furnace contains therein a neutral or reducing atmosphere. In this case, however, the atmosphere in the furnace is likely to decompose the glass on the platinum plating layer, or give rise to bubbles in the glass. Thus, it is found difficult to employ the method of controlling the atmosphere in the furnace in the manner as described above.

In view of the above, the lead wires as well as the platinum plating layer on the ceramic body are generally coated with a glass, so that the glass coating formed on the lead wires prevents the lead wires from being oxidized during firing of the glass. This method requires the procedure of removing the fired glass covering the lead wires, after the resistor is taken out from the furnace. Thus, the method suffers from considerable reduction in the productivity of the platinum-film resistor.

In the conventional method using the tubular or box-like furnace which has a relatively large heat capacity, it is difficult to control the temperature in the furnace, at a constant level in a medium to low temperature range below about 800° C. Namely, the furnace is likely to suffer from an overshoot or ringing phenomenon, deterioration in heat efficiency, and an increased firing time.

An electric heating device may be used instead of the furnace as described above. However, the electric heating device is incapable of uniformly heating the workpiece, thereby causing local variation in the heating temperature of the workpiece. The electric heating device also suffers from an extremely large heat capacity, as compared with that of the platinum-film resistor.

SUMMARY OF THE INVENTION

The present invention was developed in light of the above situations. It is therefore a first object of the present invention to provide an electric heater for heating a workpiece of a small size, such as a platinum-film resistor, which has both a portion that must be heated and a portion that must not be heated, such that only the portion which must be heated is more effectively and more rapidly heated and cooled by the present electric heater, than by the conventional heating means.

It is a second object of the invention to provide a method of heating a workpiece by means of the electric heater as described above.

The first object may be achieved according to one aspect of the present invention, which provides an electric heater for heating a workpiece, comprising at least one heat generating wire which generates heat upon application of an electric current thereto, and which has a diameter of not more than 1 mm, each of the above-indicated at least one heat generating wire having a heating portion which is formed by bending so as to at least partially define a heating space, the workpiece being positioned relative to the heating space such that the workpiece is spaced apart from the heating portion of the above-indicated at least one heat generating wire.

The electric heater constructed according to the present invention is formed by bending the heat generating wire or wires so as to define a suitable heating space therein. A workpiece to be heated is positioned relative to the heating space such that the workpiece is spaced apart from the heating portion of the heat generating wire or wires. Since the heat generating wire has a diameter of 1 mm or smaller and accordingly, has an extremely small heat capacity, the electric heater is capable of efficiently and rapidly heating and cooling only that portion of the workpiece which must be heated, even when the workpiece is small in size and has both that portion which must be heated and a portion which must not be heated. Thus, the present electric heater is able to heat only the portion of the workpiece which must be heated, in a reduced time and with an improved heat efficiency, according to a desired heating schedule, without suffering from any inconvenience caused by heating of the portion which must not be heated. Further, since the configuration of the heating portion(s) of the heat generating wire(s), i.e., the shape of the heating space can be determined as desired, following that of the portion of the workpiece which must be heated, that portion of the workpiece ca be uniformly heated by the present electric heater irrespective of the configuration of the workpiece.

In one form of the present invention, each of the above-indicated at least one heat generating wire has a pair of terminal portions connected to opposite ends of the heating portion, the terminal portions being operatively connected to an external power source.

As described above, the workpiece may have a first portion which must be heated and a second portion which must be prevented from being heated. In this case, the heating space has dimensions which are determined so that only the first portion of the workpiece is accommodated in the heating space, so that the first portion is exclusively heated by the heating portion of each heat generating wire. According to one feature of this form of the invention, the electric heater further comprises a heat radiating member for contacting the second portion of the workpiece.

The heating portion of each heat generating wire may take the form of a cylindrical coil having a plurality of cylindrical turns. In this case, the first portion of the workpiece is positioned in a cylindrical space defined by the cylindrical coil.

Alternatively, the heating portion of each heat generating wire may take the form of a rectangular coil having a plurality of rectangular turns. In this case, too, the first portion of the workpiece is positioned in a rectangular space defined by the rectangular coil.

The above-indicated at least one heat generating wire may consist of two heat generating wires. In this case, the heating portion of one of the two heat generating wires cooperates with the heating portion of the other heat generating wire to define the heating space therebetween. The heating portions of the two heat generating wires may be movable toward and away from each other.

The first object may also be achieved according to another aspect of the present invention, which provides an electric heater for heating a workpiece having a first portion which must be heated and a second portion which must be prevented from being heated, comprising (a) at least one heat generating wire which generates heat upon application of an electric current thereto, and which has a diameter of not more than 1 mm, each of the above-indicated at least one heat generating wire having a heating portion which is formed by bending so as to at least partially define a heating space, at least the first portion being accommodated in the heating space without contacting the above-indicated at least one heat generating wire, so that the first portion is heated by the heating portion of the heat generating wire or wires, and (b) an adiabatic member for supporting the second portion so that the second portion is insulated from the heat generated by the heating portion.

In the electric heater constructed as described above, the workpiece is heated such that its second portion which must not be heated is supported by the adiabatic member, and is thereby protected against heat from the surrounding space thereof. In this arrangement, even if the workpiece is heated by the heater while a part of the second portion as well as the first portion is accommodated in the heating space, only the first portion is effectively heated in a reduced time and with an improved heat efficiency as described above.

The second object may be achieved according to a further aspect of the invention, which provides a method of heating a workpiece by means of an electric heater, comprising the steps of (a) forming the electric heater from at least one heat generating wire having a diameter of not more than 1 mm, so that each heat generating wire has a heating portion which is formed by bending so as to at least partially define a heating space, (b) positioning the workpiece relative to the heating space such that the workpiece is spaced apart from the above-indicated at least one heat generating wire, and such that a portion of the workpiece is accommodated in the heating space, and (c) applying an electric current to the above-indicated at least one heat generating wire so that only the portion of the workpiece is heated by the heating portion of the heat generating wire or wires.

According to the above-described method, the heater is capable of efficiently and exclusively heating that portion of the workpiece which must be heated, even where the workpiece is small-sized and has both that portion which must be heated and a portion which must not be heated.

BRIEF DESCRIPTION OF THE DRAWINGS

The above and optional objects, features and advantages of the present invention will be better understood by reading the following description of presently preferred embodiments of the invention, when considered in conjunction with the accompanying drawings, in which.

DETAILED DESCRIPTION OF THE PREFERRED EMBODIMENT

Figure 1:
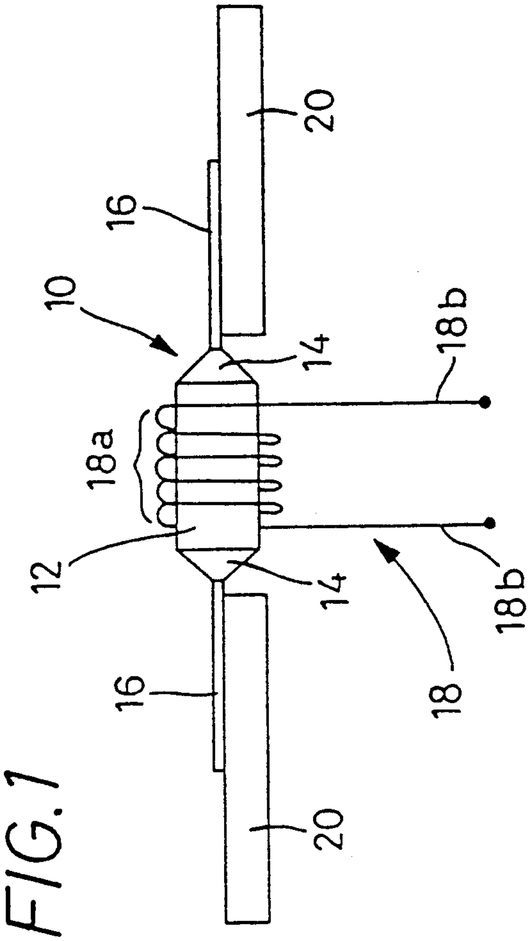
FIG. 1 is a view showing one embodiment of an electric heater according to the present invention, together with a platinum-film resistor as a workpiece to be heated by the heater.

Referring first to FIG. 1, there is shown one preferred embodiment of the present invention in the form of an electric heater 18, together with a platinum-film resistor 10 which is used as a workpiece to be heated. The platinum-film resistor 10 consists of a resistor body 12 as a first portion which must be heated, and a pair of lead wires 16, 16 as a second portion which must not be heated. The resistor body 12 is formed from a ceramic tube made of alumina, for example. The ceramic tube is plated with platinum so that a platinum layer having a predetermined thickness is formed on the circumferential surface thereof, and then suitably heat-treated to provide the platinum-plated resistor body 12. The lead wires 16, 16 are made of base metal, and are connected to axially opposite ends of the tubular resistor body 12, by means of a pair of platinum lugs 14, 14 which are formed by firing platinum paste applied to the axially opposite end faces of the resistor body 12.

The electric heater 18 constructed according to the present invention is used for firing a protective glass which covers the resistor body 12 of the platinum-film resistor 10. The heater 18 is constituted by a heat generating wire, which is made of a suitable material such as platinum, Ni-Cr alloy, and Fe-Cr alloy, that generates heat upon energization thereof. The heat generating wire has a diameter of 1 mm or smaller, preferably, 0.5 mm or smaller.

The electric heater 18 in the form of the heat generating wire as described above consists of a heating portion in the form of a cylindrical coil portion 18*a*, and two terminal portions 18*b*, 18*b* connected to opposite ends of the cylindrical coil portion 18*a*. The cylindrical coil portion 18*a* has a diameter a little larger than the outside diameter of the tubular resistor body 12 of the resistor 10, and an axial length a little shorter than that of the resistor body 12. This coil portion 18*a* is wound around the resistor body 12 at a predetermined pitch, with a suitable spacing left therebetween, as shown in FIG. 1.

In the instant embodiment, the electric heater 18 is adapted to fire the glass applied to the surface of the resistor body 12 of the resistor 10. For this purpose, the platinum-film resistor 10 is inserted through an internal cylindrical space of the cylindrical coil portion 18*a* of the heater 18, so that the resistor body 12 is placed in substantially coaxial relationship with the coil portion 18*a*, as shown in FIG. 1. In other words, the resistor body 12 is positioned at a radially central portion of the above-indicated internal cylindrical space, i.e., cylindrical heating space, which is surrounded by the heat generating wire of the coil portion 18*a* of the heater 18, such that the resistor body 12 stands apart from the coil portion 18*a*. It will be understood that the platinum-film resistor 10 as a workpiece to be heated is positioned relative to the heater 18 so that only the resistor body 12 as the above-indicated first portion is heated by the heating coil portion 18*a* of the heater 18.

With the platinum-film resistor 10 being positioned relative to the electric heater 18 as described above, an electric current is applied to the heater 18, according to a desired schedule of heat treatment. Such energization of the heater 18 is effected preferably with the lead wires 16, 16 of the resistor 10 being held in contact with respective heat radiating rods 20, 20, as shown in FIG. 1. More preferably, the heater 18 is energized while a semi-cylindrical covering member (not shown) is disposed above the coil portion 18*a* of the heater 18, with a relatively small spacing left therebetween.

Figure 2:
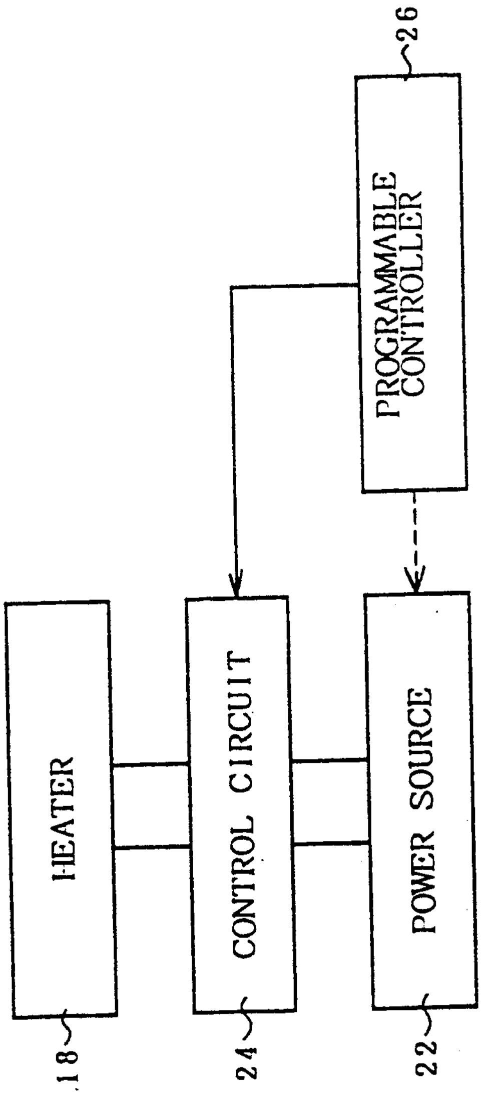
FIG. 2 is a block diagram showing an example of a current supply device for applying a controlled amount of electric current to the heater of FIG. 1, so as to energize the heater to generate heat.

Between the electric heater 18, more precisely, the terminal portions 18*b*, 18*b*, and a power source 22, there is interposed a control circuit 24 which includes a relay or a thyristor, for example. In this arrangement, a suitable amount of electric current is applied to the heater 18 by operation of the control circuit 24 under control of a programmable controller 26 connected to the circuit 24. If the power source 22 is adapted to supply a constant voltage or current, the programmable controller 26 is also used to directly control the power source 22 for supply of the constant voltage or current, as indicated by a broken line in FIG. 2.

As described above, the electric heater 18 is disposed such that only the resistor body 12 of the platinum-film resistor 10 is surrounded by the coil portion 18*a* of the heater 18. Further, the heater 18 is formed by the heat generating wire whose diameter is 1 mm or smaller, and which has a considerably small heat capacity. Therefore, the heating temperature of the heater 81 is efficiently or rapidly raised or lowered according to a change in the amount of electric current applied to the heater 18. It will be understood from the above description that the instant electric heater 18 is capable of exclusively heating the selected portion (resistor body 12) of the platinum-film resistor 10, precisely according to the predetermined schedule of heat treatment. It follows that the instant electric heater 18 is able to effectively fire the glass applied to the surface of the resistor body 12 so as to form the protective glass thereon, without causing unfavorable oxidation of the lead wires 16, 16 disposed adjacent to the resistor body 12.

In the manner as described above, the protective glass applied to the platinum-plated surface of the resistor body 12 can be fired simply by inserting the platinum-film resistor 10 through the cylindrical space of the heating coil portion 18*a* of the heater 18, and applying to the heater 18 the electric current controlled by the control circuit 24. The heater 18 does not cause unfavorable oxidation of the lead wires 16, 16. This means that the procedure for forming the protective glass on the resistor body 12 can be considerably simplified, and does not require applying a glass also to the lead wires 16, 16 for protection against oxidation of the wires during the firing operation, and removing the applied glass from the lead wires 16, 16 after the firing operation. Further, since the heater 18 having a considerably small heat capacity can be rapidly heated or cooled, the heater 18 is advantageous for its remarkably improved heat efficiency, assuring a considerably reduced time required for firing the glass on the resistor body 18. Moreover, the present electric heater 18 is free from an overshoot or ringing phenomenon, even when the heater 18 is controlled such that the heating temperature of the heater 18 is kept constant in a medium to low temperature range, more specifically, around 800° C. or lower.

Since the instant electric heater 18 itself is considerably compact or small-sized, a space for accommodating the heater 18 can be relatively small, when operated under vacuum, or in a nitrogen or hydrogen atmosphere.

As described above, the firing of the glass on the resistor body 12 is preferably effected with the heat radiation rods 20, 20 being held in contact with the lead wires 16, 16, which constitute the above-indicated second portion of the platinum-film resistor 10, i.e., the portion which must not be heated by the heater 18. This arrangement avoids an increase in the temperature of the lead wires 16, 16 during firing of the glass, thereby effectively preventing the lead wires 16, 16 from being oxidized. Further, the semi-cylindrical covering member may be disposed above the heating coil portion 18*a* of the heater 18 such that the covering member is spaced a small distance from the heater 18, as also described above. In this arrangement, the covering member serves to prevent occurrence of ascending current, whereby the resistor body 12 as the first portion which must be heated can be uniformly heated with an improved heat efficiency.

An example of the platinum-film resistor 10 as a workpiece to be heated was prepared in the following manner. At first, a ceramic tube having a diameter of 2 mm and a length of 4 mm was plated with platinum and then fired, to thereby form a platinum layer having a thickness of 0.10 μm, on the surface of the ceramic tube. Thus, the resistor body 12 having a platinum-plated surface was prepared. ON the other hand, the lead wires 16, 16 were prepared, each having a diameter of 0.15 mm and a length of 10 mm and made of an Ni-Fe alloy. Then, the lead wires 16, 16 were connected to the axially opposite ends of the resistor body 12, by means of platinum lugs 14, 14 which were formed by firing platinum paste applied to the opposite ends of the resistor body 12. A glass was applied to the resistor body 12 of the platinum-film resistor 10 produced.

Figure 3:
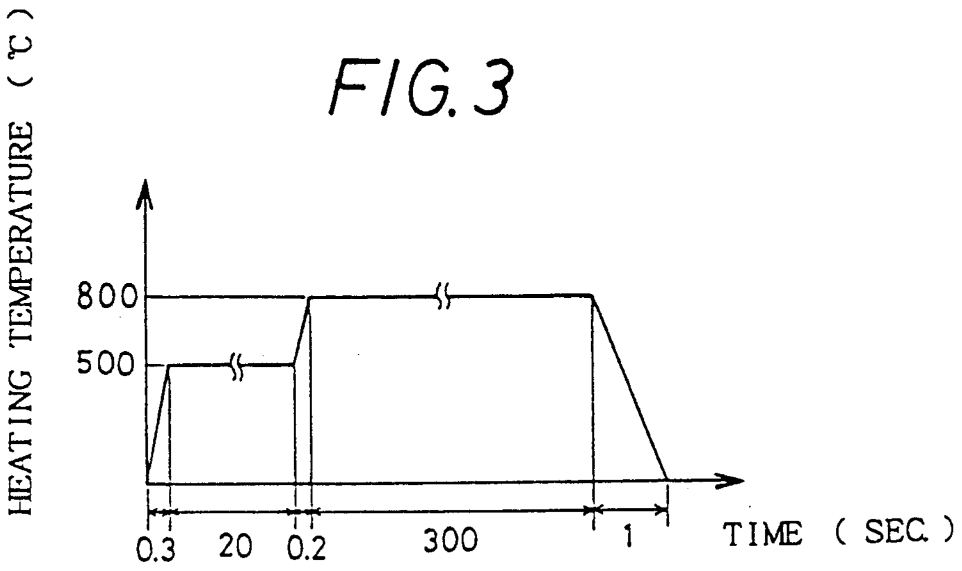
FIG. 3 is a graph showing a schedule of heat treatment by way of example, when the electric heater of FIG. 1 is used for firing a protective glass applied to the platinum-film resistor.

On the other hand, there was prepared an example of the electric heater 18 as shown in FIG. 1, which is used for firing the protective glass formed on the resistor body 12 of the platinum-film resistor 10. The electric heater 18 was formed by a platinum wire having a diameter of 0.4 mm, such that the heating coil portion 18*a* of the heater 18 has an axial length of 3 mm, and an inside diameter a little larger than the diameter of the ceramic tube. This electric heater 18 was positioned relative to the platinum-film resistor 10 as shown in FIG. 1, and then energized according to a heating schedule as shown in FIG. 3, to generate heat for firing the glass applied to the surface of the resistor body 12 of the resistor 10. After firing of the protective glass on the resistor body 12, the state of the fired glass and the degree of oxidation of the lead wires 16, 16 were observed. The observation revealed that the state of the glass after firing thereof was extremely good, and that the lead wires 16, 16 were oxidized only at their proximal portions which were not held in contact with the heat radiating rods 20, 20. Although the surfaces of the proximal end portions of the wires 16, 16 experienced a slight degree of discoloration, such oxidation had substantially no influence on the operation of the lead wires 16, 16. Further, it was recognized that the temperature in the heating space of the heater 18, i.e., in the internal cylindrical space of the coil portion 18*a*, closely followed a predetermined change in the heating temperature according to the heating schedule as shown in FIG. 3. It was also recognized that the heater 18 was controlled so as to maintain the heating temperature at 500° C., without the occurrence of overshoot or ringing.

As a comparative example, the heat treatment similar to that as described above was conducted with respect to the platinum-film resistor 10, without using the heat radiating rods 20, 20. The observation after the heat treatment revealed that the length of a portion of each lead wire 16 which experienced discoloration was increased to 3 to 4 mm. However, these discolored portions of the lead wires 16, 16 were oxidized only at their surfaces, and will not cause any problems in the practical use of the resistor 10.

Figure 4:
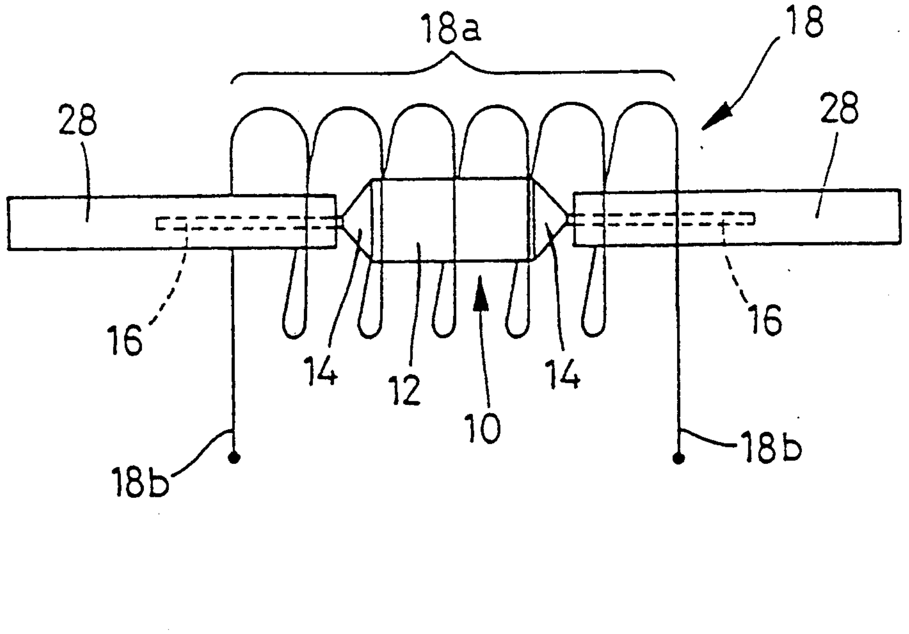
FIG. 4 is a view showing another embodiment of the electric heater of the invention, together with a platinum-film resistor as a workpiece to be heated by the heater.

Referring next to FIG. 4, there is shown another embodiment of the present invention. This embodiment is different from the preceding embodiment, only in the relationship between the lengths of the resistor body 12 of the platinum-film resistor 10, and the coil portion 18*a* of the electric heater 18.

More specifically, the heating coil portion 18*a* of the heater 18 of the present embodiment has a length which is a little larger than that of the resistor body 12 of the resistor 10. Upon firing of the glass applied to the surface of the resistor body 12, a portion of the lead wires 16, 16 adjacent to the resistor body 12 as well as the resistor body 12 is positioned within the heating space of the heater 18 (internal space of the coil portion 18*a*). In other words, the heating space of the heater 18 extends over a part of the second portion 16 of the resistor 10, which must not be heater, as well as the first portion 12 which must be heated.

In the instant embodiment, the lead wires 16, 16 of the resistor 10 are inserted into respective adiabatic pipes 28, 28 made of alumina, for example, as shown in FIG. 4. In this arrangement, the protective glass is fired by the heater 18 as described above while the lead wires 16, 16 supported by the adiabatic pipes 28, 28 are protected against heat from the surrounding space thereof. As a result, the heater 18 of the instant embodiment is able to provide the similar effects as provided in the preceding embodiment.

It is possible to insert a heat radiating rod into each of the adiabatic pipes 28, 28, such that the heat radiating rod is held in contact with the corresponding lead wire 16 during the firing operation of the heater 18. This arrangement effectively avoids an increase in the temperature of the lead wires 16, 16, and accordingly prevents the oxidation of the wires 16, 16.

It is also possible to water-cool the adiabatic pipes 28, 28, for preventing the oxidation of the lead wires 16, 16.

While the present invention has been described in detail in its presently preferred embodiments referring to the accompanying drawings, it is to be understood that the invention is not construed to be limited to the details of the illustrated embodiments but that the invention may be embodied with various changes, modifications and improvements, which may occur to those skilled in the art, without departing from the spirit and scope of the invention as defined in the appended claims.

Figure 5:
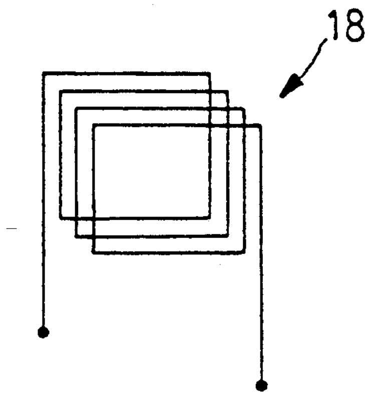
FIGS. 5, 6 and 7 are perspective views showing further embodiments of the electric heater according to the present invention.
Figure 6:
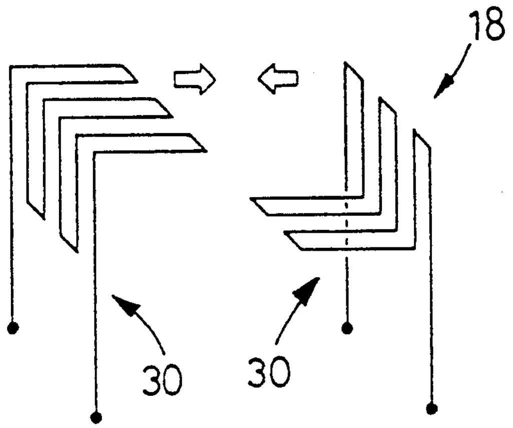
Figure 7:
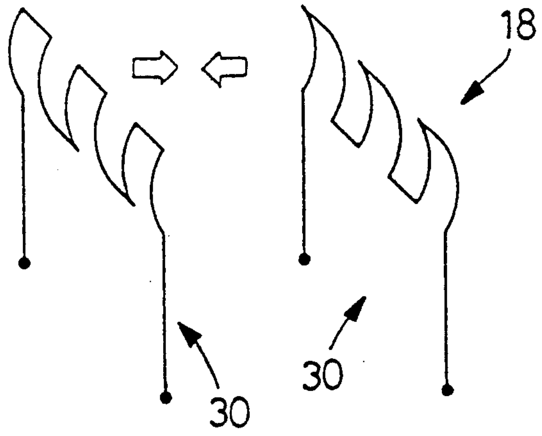

While the electric heater 18 is formed by the heat generating wire having a cylindrical coil with cylindrical turns in the illustrated embodiments, the heater 18 may be formed by a heat generating wire as shown in FIG. 5, which has a rectangular heating coil portion with rectangular turns. It is also possible to use a plurality of heater elements 30 which are formed by bending respective heat generating wires in appropriate directions. The thus produced heater elements 30 are disposed to form the electric heater 18, as shown in FIGS. 6 and 7. These heater elements 30 are disposed movably toward and away form each other, as necessary. With the heater elements 30 moved toward each other as indicated by arrows of FIG. 6 and 7, the appropriate heating space of the heater 18 is formed between the heating portions of the elements 30. This arrangement makes it much easier to place the workpiece to be heated in the heating space of the heater 18, which leads to simplification of the heating procedure.

In the illustrated embodiments, the electric heater 18 is adapted to heat the platinum-film resistor 10 as the workpiece to be heated. However, it will be readily understood that the heater according to the present invention may be used to heat at workpiece other than the platinum-film resistor. In any case, the configuration of the heat generating wire or wires of the heater may be suitably determined depending upon the position of the above-indicated first portion of the workpiece. In the case where the heat generating wire is relatively long in light of its strength, and where the heater cannot maintain its configuration on its own strength, a portion of the heater may be supported by an adiabatic ceramic fiber or fibers.

What is claimed is:

1. An electric heater for heating a glass coating on a resistor body of a resistor thereby forming a protective glass covering, said resistor having first and second lead wires, each of which is connected to respective opposite ends of said resistor body, the electric heater comprising:

at least one heat generating wire which generates heat upon application of an electric current thereto, each of said at least one heat generating wire having a bent heating portion whose shape at least partially defines a heating space, said heating portion having a length which is smaller than a length of said glass coating so that only said glass coating, except end portions thereof, is accommodated in said heating space, said heating portion being further dimensioned so that said glass coating is spaced apart from said at least one heat generating wire;

a pair of terminal portions connected to opposite ends of said heating portion, for connecting said heating portion to an external power source; and first and second heat radiating members contacting said first and second lead wires, respectively, so that heat transferred to said first and second lead wires from said glass coating and said resistor body is radiated through said first and second heat radiating members.

2. An electric heater according to claim 1, wherein said heating portion of said each heat generating wire takes the form of a cylindrical coil having a plurality of cylindrical turns, said glass coating of said resistor body being positioned in a cylindrical space defined by said cylindrical coil.

3. An electric heater according to claim 1, wherein said heating portion of said each heat generating wire takes the form of a rectangular coil having a plurality of rectangular turns, said glass coating of said resistor body being positioned in a rectangular space defined by said rectangular coil.

4. An electric heater according to claim 1, wherein said at least one heat generating wire consists of two heat generating wires, said heating portions of one of said two heat generating wires cooperating with said heating portion of the other heat generating wire to define said heating spaced therebetween.

5. An electric heating according to claim 4, wherein said heating portions of said two heat generating wires are movable toward and away from each other.

6. The electric heater of claim 1, wherein each of said at least one heat generating wire has a diameter of not more than 1 mm.

7. The electric heater of claim 1, wherein said first and second heat radiating members consist of a pair of insulative tubes which are disposed adjacent said pair of lead wires and extend along an axial direction of said resistor body.

8. The electric heater of claim 1, wherein said pair of lead wires is formed of a base metal.

9. An electric heater for heating a glass coating on a resistor body of a resistor thereby forming a protective glass covering, said resistor having first and second lead wires, each of which is connected to respective opposite ends of said resistor body, comprising:

at least one heat generating wire which generates heat upon application of an electric current thereto, said heat generating wire having a bent heating portion whose shape at least partially defines a heating space, at least said glass coating being accommodated in said heating space without contacting said heat generating wire, so that said glass coating is fired by said heating portion; and first and second adiabatic members disposed adjacent said heat generating wire and around said first and second lead wires, respectively, such that said first and second lead wires are substantially completely insulated from the heat generated by said heating portion.

10. The electric heater of claim 9, wherein said heating portion fires said first portion at temperatures ranging from 500°-800° C.

11. The electric heater of claim 9, wherein said adiabatic member consists of an insulative tube which is disposed completely around said second portion and extends along an axial direction of said resistor body.

12. The electric heater of claim 9, wherein said heat generating wire has a diameter of not more than 1 mm.

13. The electric heater of claim 9, wherein said pair of lead wires are formed of a base metal.

14. A method of heating a glass coating on a resistor body of a resistor thereby forming a protective glass covering, said resistor having first and second lead wires, each of which is connected to respective opposite ends of said resistor body, the method comprising the steps of:

forming at least one heat generating wire which generates heat upon application of an electric current thereto, so that said heat generating wire has a bent heating portion whose shape at least partially defines a heating space, and so that said heating portion has a length which is smaller than a length of said glass coating;

forming a pair of terminal portions at opposite ends of said heating portion for connecting said heating portion to an external power source;

forming a pair of heat radiating members near said heating portion;

positioning said resistor relative to said heating space such that said glass coating is spaced apart from said heat generating wire, only said glass coating except for end portions thereof is accommodated in said heating space and said pair of lead wires are supported by said heat radiating members;

applying an electric current to said heat generating wire such that only said glass coating is fired by said heating portion, and such that heat transferred to said lead wires from said glass coating and said resistor body is radiated through said heat radiating members; and removing said resistor from said heating space.

15. The electric heater of claim 14, wherein said pair of lead wires are formed of a base metal.

16. A method of heating a glass coating on a resistor body of a resistor thereby forming a protective glass covering, said resistor having a pair of lead wires, each of which is connected to respective opposite ends of said resistor body, comprising the steps of:

forming at least one heat generating wire which generates heat upon application of an electric current thereto, so that said heat generating wire has a bent heating portion whose shape at least partially defines a heating space;

forming a pair of adiabatic members near said heating portion;

positioning said resistor relative to said heating space such that said glass coating is spaced apart from said heat generating wire and said pair of lead wires are disposed within said adiabatic members;

applying an electric current to said heat generating wire such that said adiabatic members substantially completely insulate said lead wires from heat generated by said heating portion; and removing said resistor from said heating space.

17. The electric heating of claim 16, wherein said pair of lead wires are formed of a base metal.

* * * * *